(12) United States Patent
Kumar et al.

(10) Patent No.: US 6,896,806 B2
(45) Date of Patent: May 24, 2005

(54) BIOLOGICAL PROCESS FOR COLOR REDUCTION OF PULP AND PAPER EFFLUENT

(75) Inventors: Rita Kumar, New Delhi (IN); Anil Kumar, New Delhi (IN); Deepa Kachroo Tiku, New Delhi (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 10/393,354

(22) Filed: Mar. 21, 2003

(65) Prior Publication Data

US 2004/0018608 A1 Jan. 29, 2004

Related U.S. Application Data

(60) Provisional application No. 60/365,808, filed on Mar. 21, 2002.

(51) Int. Cl.$^7$ .............................. C02F 3/00; C12N 1/12
(52) U.S. Cl. ...................... 210/620; 210/614; 210/917; 210/928; 435/252.1
(58) Field of Search ................................ 210/928, 917, 210/601; 435/252.1

*Primary Examiner*—Chester T. Barry
(74) *Attorney, Agent, or Firm*—Foley & Lardner LLP

(57) ABSTRACT

The present invention relates to a bacterium strain of accession no. MTCC 5099, a process for the preparation of innoculum of the said strain, and a process for the reduction of color from pulp mill effluent using the above said innoculum, which comprises steps of inoculating appropriate aliquots of the pulp and paper mill effluent with the cell slurry obtained, incubating the mixture at about 37° C. at about 100 rpm for time duration ranging between 24–48 hours, assessing color and total lignin levels to determine the color removal efficiency of the above said bacterium

7 Claims, No Drawings

BIOLOGICAL PROCESS FOR COLOR REDUCTION OF PULP AND PAPER EFFLUENT

CROSS REFERENCE TO RELATED PATENTS AND PATENT APPLICATIONS

The present application claims the benefit of provisional application No. 60/365,808, filed Mar. 21, 2002.

FIELD OF THE PRESENT INVENTION

The present invention relates to a bacterium strain of accession no. MTCC 5099, a process for the preparation of inoculum of the said strain, and a process for the reduction of colour from pulp mill effluent using the above said inoculum, which comprises steps of inoculating appropriate aliquots of the pulp and paper mill effluent with the cell slurry obtained, incubating the mixture at about 37° C. at about 100 rpm for time duration ranging between 24–48 hours, assessing colour and total lignin levels to determine the colour removal efficiency of the above said bacterium

BACKGROUND AND PRIOR ART REFERENCES OF THE PRESENT INVENTION

The problem of colour removal from pulp and paper mill waste has been a subject of great consideration and investigation in the last few decades. An estimated two trillion gallons of wastewaters are discharged annually by the pulp and paper industry in major paper-producing countries and much of this effluent is highly coloured. (Joyce et al., 1983).

The brownish colour of the wastewater is mainly organic in nature and primarily attributable to lignin degradation products formed during various pulping and bleaching operations (Srivastava et al., 1984, Dilek et al., 2000). The other colour-imparting agents are wood-extractives, tannins, resins and synthetic dyes.

Colour was never thought to be a major problem, being classified as a non-conventional pollutant. The reasons for colour regulations at some places are said to be, protection of fisheries or aesthetic considerations. Secondly, discharge of coloured pulping effluents to the receiving waters, inhibits photosynthetic activity of aquatic biota by reducing the penetration of sunlight, besides having direct toxic effects on biota.

The colour compounds also chelate metal ions and may impart contamination by heavy metals. Recently, the colour causing organic compounds have also been implicated in the appearance of blue-green algal blooms (Paerl, 1982; Kuenzler et al., 1982; Witherspoon & Pierce, 1982). It is therefore, imperative that the colour present in pulp and paper mill effluents be removed, before being discharged into receiving waters.

There are two general strategies for the removal of colour from the effluent of a pulp & paper mill:

1) Conventional end of pipe treatment
2) Modification of the pulp and paper manufacturing process so that less colour is produced The following are the conventionally used colour removing technologies:

Secondary treatment: the effluents are treated with conventional activated sludge method. However, conventional biological treatment systems cannot remove colour (Yosefian et al., 2000).
Enzyme pre-treatment
Resin separation and ion exchange
Aluminium oxide
Adsorption on wood
Membrane processes
Irradiation
Electrolytic process
Activated carbon
Land treatment
Ozone At this point, no single colour removal technology has been identified as the most effective. Since all the above-cited technologies are cost-intensive, they would have adverse economic impact on the mill involved. Moreover, chemical treatment processes add up to the ever-increasing concentration of chemicals in the environment (Kapdam et al., 2000).

In principle, decolorization is achievable using one or a combination of the following methods;

Adsorption
Filtration
Precipitation
Chemical degradation
Photodegradation and
Biodegradation Rohella et al., 2001 used polyelectrolytes (commercially available) for removing colour from pulp mill effluents. However, the cost-benefit analysis of this treatment has not yet been worked upon and hence this type of technology is not viable. However, since the polyelectrolytes rely on ionic charge of the effluent, the colour reducing ability will be highly variable, considering the enormous fluctuations occurring in the composition of the wastewater.

The majority of colour removal techniques work either by concentrating the colour into a sludge or by the partial breakdown or complete breakdown of the colored molecule (Willmott et al, 1998). However, the colour and chemical composition of the pulp mill effluents are usually subject to both daily process as well as seasonal variations. A single, universally applicable end-of-pipe solution has therefore not emerged till date.

General physico-chemical colour removal methods such as chemical precipitation, rapid sand filtration, membrane processes and adsorption have been developed (Springer, 1985). Adsorption and membrane processes, although are efficient, but expensive (Manjunath and Mehrotra, 1981).

Application of electrochemical methods is another way to treat the wastewaters from the cellulose paper production (Christoskova and Lazarov, 1988). This method guarantees high treatment efficiency but its effectiveness depends upon the types of electrodes, the construction of electrocoagulators and the conditions under which the process is run.

Chemical precipitation, using alum, ferric chloride and lime has also been studied extensively (Lathia and Joyce, 1978; Dugal et al, 1976; Joyce et al, 1979; Srivastava et al, 1984; Beulker and Jekel, 1993; Stephenson & Duff, 1996). In spite of short retention times and low capital costs, there are some drawbacks reported, such as high cost of chemicals for precipitation as well as for pH adjustment, voluminous sludge production due to heavy dosages, problems associated with dewatering and disposing of generated sludge and high residual cation levels, so that their colour remains in the supernatant (Stephenson and Duff, 1996; Srivastava et al, 1984).

In theory, biological treatment gives the ideal solution to colour removal as less sludge is produced as compared to chemical treatments. Lower daily running costs are also incurred. Among the biological systems, white-rot fungi have been extensively researched upon, for their capability to degrade lignin which forms an important and major component of the pulp and paper effluents (Feijoo et al., 1995). Certain workers have shown that the pellets of white-rot fungi, under specific conditions of incubation, strongly adsorb colour and AOX from the kraft bleach plant effluent (Jaspers et al., 1996).

Raghu Kumar et al., 1996, showed that marine fungi could also be utilized for colour removal from bleached plant effluent. One of the strain was reported to give 74% decolorization at alkaline pH over a period of 14 days. Several other researchers have also reported partial decolorization by white-rot fungi (Eaton et al, 1980; Livernoche et al, 1983; Pronty, 1990; Gokcay and Dilek, 1994). Gokcay and Dilek (1994) have pointed out that due to the need for high glucose concentrations by the fungus, this treatment is economically non-feasible. They have also reported that the fungi were not effective when bleaching effluents were present.

Dilek et al., 1999 have reported the decolorization of pulping effluents using a mixed culture algae. A combination of aerobic-anaerobic treatment has been used by Vidal et al. White-rot fungi excreting several extracellular oxidative enzymes including Lignin peroxidase, Manganese peroxidase and laccases were used for decolorizing bleach kraft pulp mill effluents. Up to 64% colour was removed by applying aerobic-anaerobic treatment followed by enzyme treatment.

Till date, there are almost no reports regarding the utilization of pure bacterial cultures for decolorization of pulping effluent. The novelty of the present invention is the application of pure cultures of bacteria, isolated from natural habitat, for removing colour of the pulp and paper wastewaters in an industrially and economically viable fashion.

OBJECTS OF THE PRESENT INVENTION

The main object of the present invention is to provide a process for the aerobic treatment of pulp mill wastewater for colour reduction.

Another object of the present invention is to provide a bacterial strain for colour reduction of paper and pulp effluent.

Still another object of the present invention is to develop an inoculum of the strain for colour reduction of paper and pulp effluents.

SUMMARY OF THE PRESENT INVENTION

The present invention relates to a bacterium strain of accession no. MTCC 5099, a process for the preparation of inoculum of the said strain, and a process for the reduction of colour from pulp mill effluent using the above said inoculum, which comprises steps of inoculating appropriate aliquots of the pulp and paper mill effluent with the cell slurry obtained, incubating the mixture at about 37° C. at about 100 rpm for time duration ranging between 24–48 hours, assessing colour and total lignin levels to determine the colour removal efficiency of the above said bacterium

DETAILED DESCRIPTION OF THE PRESENT INVENTION

The present invention relates to a bacterium strain of accession no. MTCC 5099, a process for the preparation of inoculum of the strain, and a process for the reduction of colour from pulp mill effluent using the above said inoculum, which comprises steps of inoculating appropriate aliquots of the pulp and paper mill effluent with the cell slurry obtained, as claimed in claim 2, for colour reduction studies along with a control flask containing effluent sample without any added inoculum, incubating the flasks set up in step (a) at 37° C./100 rpm for 48 hours, withdrawing samples from the above flasks in 50 ml aliquots and processing them for assessing colour and Total lignin levels analyzing the colour removal efficiency of the above said bacterium In still another embodiment of the present invention, wherein a bacterium strain of Accession No. MTCC 5099.

In still another embodiment of the present invention, wherein A strain as claimed in claim 1, wherein the strain is gram -ve.

In still another embodiment of the present invention, wherein A strain as claimed in claim 1, wherein the strain is short rods.

In still another embodiment of the present invention, wherein a process for the preparation of inoculum of the strain of claim 1, said process comprises of:

i) isolating a bacterium from activated sludge collected from the effluent treatment plant of a pulp and paper mill, ii) culturing the said bacterium on nutrient agar media containing 0.1% w/v each of lignin, tannin and vanillin to get pure cultures, iii) inoculating the said bacterium in nutrient broth containing 0.01% Tween 80 to obtain starter culture, iv) culturing the above bacterium for obtaining required biomass by inoculating appropriate aliquot of nutrient broth, with the starter culture and incubating the above medium at 37° C./100 rpm for 16–18 hours, v) centrifuging the resulting culture, after attaining an optical density of 1.5–2.0, to obtain pellet, washing the collected pellet by dissolving in $PO_4^{-3}$ buffer, 0.05M, pH 6.8, recentrifuging the pellet, and vi) collecting the pellet obtained from step (e), dissolving in 10 ml of $PO_4^{-3}$ buffer, 0.05M, pH 6.8, to obtain cell slurry for treatability studies.

In still another embodiment of the present invention, wherein the inoculum for using in colour reduction experiments is obtained by inoculating the above said bacterium in nutrient broth containing 0.01% Tween 80 to obtain starter culture.

In still another embodiment of the present invention, wherein the above said starter culture is used for obtaining the required inoculum by inoculating appropriate aliquot of nutrient broth, with the starter culture and incubating the above medium at 37° C./100 rpm for 16–18 hours;

In still another embodiment of the present invention, wherein the resultant culture is centrifuged at appropriate rpm, preferably 6000 rpm for a period of 20 minutes at 4° C.

In still another embodiment of the present invention, wherein the resultant pellet is washed by dissolving in $PO_4^{-3}$ buffer, 0.05M, pH 6.8 and recentrifuging the pellet.

In still another embodiment of the present invention, wherein the resultant pellet is dissolved in 10 ml of $PO_4^{-3}$ buffer, 0.05 M, pH 6.8, to obtain inoculum for colour reduction studies;

In still another embodiment of the present invention, wherein coloour from pulp mill effluent using the above said inoculum, as claimed in claim 2 which comprises:

i) inoculating appropriate aliquots of the pulp and paper mill effluent with the cell slurry obtained, as claimed in claim 2, for colour reduction studies along with a control flask containing effluent sample without any added inoculum;

ii) incubating the flasks set up in step (a) at 37° C./100 rpm for 48 hours;

iii) withdrawing samples from the above flasks in 50 ml aliquots and processing them for assessing colour and Total lignin levels, iv) analysing the colour removal efficiency of the above said bacterium by comparing the colour levels of the effluent treated with the bacterium, as claimed in claim 2, with the colour level of control sample after 24 and 48-hour intervals, v) checking the viability of the above said culture in the effluent by culturing the same on nutrient agar medium and calculating CFU/ml.

In still another embodiment of the present invention, wherein the viability of the above said culture is checked by plating dilutions of sample taken from the experiment to obtain countable colonies and calculating CFU/ml of the same after 24 and 48 hour intervals.

In still another embodiment of the present invention, wherein A process as claimed in claims 1 to 9, wherein an aerobic, biological decolorization process is defined using a bacterial isolate, obtained from activated sludge of a pulp and paper mill ETP, which gives up to 55% reduction in colour levels of the given effluent.

In still another embodiment of the present invention, wherein the strain shows color reduction of 55% in 24 hrs.

In still another embodiment of the present invention, wherein the strain shows color reduction of 60% in 48 hrs.

In still another embodiment of the present invention, wherein the ratio of equivalent to biomass is about 1:1.

In still another embodiment of the present invention, wherein the strain is viable after the color reduction.

In still another embodiment of the present invention, wherein the invention provides a biological process for the reduction of colour from pulp and paper mill effluent. Also disclosed is a bacterial strain isolated from a specific source, capable of reducing colour from pulp and paper effluent. The said bacterial isolate was able to reduce the colour of the effluent.

In still another embodiment of the present invention, wherein The present invention relates to a biological process for colour reduction from pulp and paper mill effluent using an aerobic bacterial strain isolated from specific source from the pulp and paper mill.

In still another embodiment of the present invention, wherein the present invention provides a process for the reduction of from a pulp mill effluent using aerobic treatment process. An aerobic bacterial strain was isolated from a specific source from the pulp and paper mill and used for decolorization of the pulp mill effluent.

In still another embodiment of the present invention, wherein The bacterial isolate according to the present invention is presently deposited at IGIB as CBTCC/ and its identification is underway.

In still another embodiment of the present invention, wherein This bacterial isolate facilitates the reduction of colour from pulp and paper effluent.

In still another embodiment of the present invention, wherein The bacterium described in the said invention is isolated from activated sludge of effluent treatment plant of a pulp and paper mill. 5.0 grams of homogenised activated sludge taken from effluent treatment plant of pulp and paper mill is inoculated in the enrichment medium. The enrichment medium consists of 100 ml of sludge infusion, 25 ml of sterile nutrient broth and 0.1% (w/v) each of lignin (Alkali lignin-Aldrich, USA), vanillin and tannin (Sigma). The pH is adjusted to 6.8±0.2.

In still another embodiment of the present invention, wherein The sludge extract is prepared by boiling a mixture containing 300 ml of sludge in 1200 ml of triple distilled water for about 30 minutes. The infusion was cooled, centrifuged and coarse filtered.

The final filtrate obtained is autoclaved at 121° C., 15 psi for 20 minutes and used for preparing the enrichment medium. The enrichment medium inoculated with activated sludge is incubated at 37° C. for 24–48 hours to obtain an enriched culture.

In still another embodiment of the present invention, wherein The enriched culture is serially diluted to $10^{-12}$ using 0.05M $NaH_2PO_4$—$Na_2HPO_4$ buffer, pH 7.0. Stock solutions of lignin, vanillin and tannin are prepared. Nutrient broth containing 2% agar is prepared and 0.2% (v/v) each of lignin, vanillin and tannin are added from their stock solutions. The serially diluted inoculum is then plated and incubated at 37° C. for 24–48 hours. Single isolated colony is picked and streaked on a fresh plate in the same medium. The above step is repeated twice, till pure colonies are obtained.

In still another embodiment of the present invention, wherein The above mentioned bacterium is inoculated with the help of sterile nichrome loop into 15–20 ml sterile nutrient broth (NB) containing (per litre), 5.0 g peptic digest of animal tissue, 5.0 g of sodium chloride, 1.5 g of beef extract, 1.5 g of yeast extract and 0.2 ml Tween-80. The culture is incubated at 37° C. for approximately 16–18 hours in an incubator shaker. For gentle shaking, the incubator shaker is maintained at an appropriate rpm, preferably 100 rpm. After sufficient growth is obtained, the broth was stored at 4° C. till further use. 250 ml of sterile NB is inoculated with 250 μof the above prepared starter culture.

In still another embodiment of the present invention, wherein The flask is kept for incubation at 37° C./100 rpm for 16–18 hours till an optical density (650 nm) of 1.5–2.0 is achieved. The cells are harvested by centrifuging at an appropriate rpm, preferably 6000 rpm for 20 minutes. The resultant pellet is washed by dissolving in minimum quantity of phosphate bufer, 0.05M, pH 6.8 and recentrifuged using the same rpm and time conditions. During centrifugation, the temperature is maintained at 4° C. The pellet thus obtained, is resuspended in minimum volume of phosphate buffer, 0.05M, pH 6.8, preferably 10 ml and vortexed to make a homogeneous suspension to be used for reducing colour from the pulp and paper effluent.

In still another embodiment of the present invention, wherein For setting up the colour reduction experiments, 250 ml of sample is taken in screw-capped conical shake flasks. The inoculum is added to the effluent sample after checking the pH of the effluent to be preferably around 7.0. Control flask which does not contain any added inoculum is also maintained for comparison. The flasks are incubated at 37° C./100 rpm for a period of 48 hours.

In still another embodiment of the present invention, wherein For analysing the colour reduction efficiency as well as the total lignin levels of the above bacterium, approximately 50 ml of samples are withdrawn. The samples are prepared for analysis by centrifuging them at appropriate rpm, preferably 8000 rpm for 30 minutes at 4° C. The supernatant is then passed through 0.45μ filters (Millipore). For measuring the colour levels, pH of the samples is adjusted to 7.6 and optical density measured at 465 nm as described in NCASI colour estimation method. The total lignin assay is also carried out by the Modified Pearl Benson method.

In still another embodiment of the present invention, wherein For assessing the viability of the culture during the entire experiment, sample is diluted serially and plated on nutrient agar medium and incubated at 37° C., overnight in an inverted position. The colonies were counted and Colony Forming Units/ml (CFU/ml) calculated.

In still another embodiment of the present invention, wherein the invention further provides a process for the preparation of inoculum of the said bacterium and using it for reduction of colour from pulp and paper industrial effluent, which comprises:

a) isolating a bacterium from activated sludge collected from the effluent treatment plant of a pulp and paper mill;

b) culturing the said bacterium on nutrient agar media containing 0.1% w/v each of lignin, tannin and vanillin to get pure cultures;

c) inoculating the said bacterium in nutrient broth containing 0.01% Tween 80 to obtain starter culture;

d) culturing the above bacterium for obtaining required biomass by inoculating appropriate aliquot of nutrient broth, with the starter culture and incubating the above medium at 37° C./100 rpm for 16–18 hours;

e) Centrifuging the resulting culture, after attaining an optical density of 1.5–2.0, to obtain pellet, washing the collected pellet by dissolving in $PO_4^{-3}$ buffer, 0.05M, pH 6.8, recentrifuging the pellet;

f) collecting the pellet obtained from step (e), dissolving in 10 ml of $PO_4^{-3}$ buffer, 0.05M, pH 6.8, to obtain cell slurry for treatability studies;

g) inoculating appropriate aliquots of the pulp and paper mill effluent with the cell slurry obtained in step (f) for colour reduction studies along with a control flask containing effluent sample without any added inoculum;

h) incubating the flasks set up in step (g) at 37° C./100 rpm for 48 hours;

i) Withdrawing samples from the above flasks in 50 ml aliquots and processing them for assessing colour and total lignin levels;

j) Analysing the colour removal efficiency of the above said bacterium by comparing with the colour level of control sample after 24 and 48-hour intervals;

k) checking the viability of the above bacterium in the effluent by colony counting method and calculating the CFU/ml after 24 and 48-hours.

In an embodiment of the present invention, the bacterium is isolated from activated sludge collected from the effluent treatment plant of a pulp and paper mill.

In another embodiment of the present invention, the above mentioned bacterium is inoculated in nutrient broth containing 0.01% Tween 80 to obtain the starter culture.

In another embodiment of the present invention, the culture of the bacterium is prepared by inoculating nutrient broth with starter culture.

In another embodiment of the present invention, the incubation of the bacterial strains is carried out by gentle agitation at 100 rpm.

In an embodiment of the present invention, the growth of the incubated bacterial strains is carried out at a temperature of 37° C. for a period of 16–18 hours.

In another embodiment of the present invention, the said bacterium was centrifuged at appropriate rpm preferably 6000 rpm for a period of approximately 20 minutes at 4° C., after achieving an optical density of approximately 1.5–2.0.

In a further embodiment of the present invention, the resultant pellet is washed by dissolving in minimum quantity of phosphate buffer, 0.05M, pH 6.8 and recentrifuged using the same rpm and time conditions. During centrifugation, the temperature is maintained at 4° C.

In a further embodiment of the present invention, The pellet thus obtained, is resuspended in minimum volume of phosphate buffer, 0.05M, pH 6.8, preferably 10 ml and vortexed to make a homogeneous suspension.

In one of the embodiment of the present invention, the cell slurry obtained above is used for inoculating the effluent samples for reducing colour.

The invention further provides a method for the reduction of colour levels from a pulp and paper mill effluent.

In another embodiment of the present invention, the flasks containing the above inoculum are incubated at 37° C. at 120 rpm for 48 hours.

In a further embodiment of the present invention, the reduction in colour and total lignin levels are observed over a period of 48 hours.

In another embodiment of the present invention, the culture is grown on plates containing nutrient agar medium for viability of the bacterium in the said effluent.

As described in the provisional patent, the bacterial consortia were able to reduce colour of the effluent over a period of five days. However, later studies were performed to reduce the retention time (make the process faster) as well as to enhance the extent of colour reduction of the effluent. Approximately 58% reduction in the colour levels within a period of 24 hours by a single bacterial isolate was observed, which is definitely better than the earlier 51% reduction in 3 to 5-days period in case of consortia. Therefore, in the complete patent specification, the results obtained by using the individual bacterial isolate have been presented; being markedly better than those obtained by the bacterial consortia.

2. The culture has been already sent for deposit to IMTECH in the international depository and number shall be allotted by Mar. 17, 2003.

3. We would like to claim for only the one bacterial isolate which has repeatedly given best results as given in table 5 and 8 of complete specification.

The strain of the instant Application is deposited in MTCC, Chandigarh INDIA and the accession o. is MTCC 5099. The strain is mentioned as bacterial strain Bacterium B4 in the specification at several places.

The invention of the instant Application is further elaborated in the form of examples. However, these examples merely substantiate the invention and do not construe to limit the scope of the invention

EXAMPLE I

Bacteria were isolated from wastewater emerging from both inlet as well as outlet of Effluent Treatment Plant. The pH of the effluent was checked and found to be 7.6±0.2. Filtered and autoclaved wastewater was used as media for isolating autochthonous bacteria in different percentages viz., 100%, 80%, 50%, 30% and 10% using mineral salts medium (MSM). The composition of the MSM used was as follows:

| | |
|---|---|
| $K_2HPO_4$ | 5 mM |
| $KH_2PO_4$ | 5 mM |
| $MgSO_4 \cdot 7H_2O$ | 1 mM |

-continued

| | |
|---|---|
| EDTA | 0.3 mM |
| ZnSO$_4$.7H$_2$O | 0.01 mM |
| MnSO$_4$.7H$_2$O | 0.02 mM |
| CuSO$_4$.7H$_2$O | 0.004 mM |
| FeSO$_4$.7H$_2$O | 0.1 mM |
| NaMoO$_4$.2H$_2$O | 0.004 mM |
| (NH$_4$)$_2$SO$_4$.7H$_2$O | 5 mM |
| pH | 7.0 ± 0.2 |

To 100 ml aliquots of Nutrient Broth (NB), 1 ml each inlet as well as outlet of wastewater was added and kept at 37° C./24–48 hrs for enrichment.

Effluent-MSM plates were prepared using 2% agar as solidifying agent. The plates were kept for solidification and inverted till further use. Serial dilution plating was carried out by serially diluting the enriched inocula till a dilution of 10–12. Serial dilution was carried out by taking 9 ml aliquots of Na2HPO4—NaH2PO4 buffer (pH 6.8, 0.05 M) and inoculating 1 ml of enriched inoculum in the first vial, vortexing and taking 1 ml from this vial and diluting the next vial with it, till a $10^{-12}$ dilution was obtained, These vials were then used for plating on to the effluent MSM plates.

100 μl of the above dilutions were placed on the different Effluent—MSM plated and spread plated with the help of a sterile glass spreader. All plates were prepared in duplicates and incubated for 24–48 hours at 37° C. Colonies appearing on these plates were marked according to morphological differences and selected for further purification.

Colonies exhibiting different morphological appearance were picked with sterile inoculating needle and streaked on plates containing the respective growth media. After two to three repetitive subculturing, purified isolates were obtained which were tested for purity and stored as slants and stabs in their respective media.

Loopful of cultures were taken and inoculated in sterile aliquots of Nutrient Broth, vortexed and kept for incubation at 37° C./120 rpm for 16–18 hrs. Checked the optical density of these mother cultures at 650 nm.

Thirty-five morphologically different bacteria were selected for ther screening their ability to reduce colour from pulp mill wastewater. 100 ml sterile NB was inoculated with 100 μl of respective mother cultures and incubated at 37° C./120 rpm for 16–18 hours. The initial and final optical densities at 650 nm were noted. Cultures were harvested at an OD$_{650}$ of 1.5–2.0 by centrifuging at 6000 rpm for 20 minutes at 4° C. The pellet obtained was washed twice using sterile phosphate buffer (pH 6.8 0.05 M) and resuspended in small volume of the same. This suspension was then used for treatability assay in a ratio of 1:1, i.e., 100 ml of effluent sample was treated with pellet obtained from 100 ml of culture media.

The colour removal experiment was carried out in batch culture in conical shake flasks at 37° C. at 120 rpm for a period of five days. Colour intensities were measured at 450 nm using NCASI optical density method on zero day, third day and fifth days. 13 bacteria gave a reduction of 50% and more on the fifth day (Table 1).

EXAMPLE II

The thirteen individual bacteria exhibiting more than 50% colour reduction were selected and nine different bacterial consortia were formulated using random combinations.

Individual cultures constituting the formulated consortia were independently grown in nutrient broth by inoculating 100 μl of actively growing cultures in each flask. Cultures were incubated at 37° C./16–18 hrs at 120 rpm until an optical density of 1.5–2.0 was achieved. The cultures were then pooled together according to the consortial composition. Optical density at 650 nm of the pooled culture was measured. The cells of the resulting consortia were harvested by centrifuging at 6000 rpm for 20 minutes at 4° C. and was washed twice with Na$_2$HPO$_4$—NaH$_2$PO$_4$ buffer (pH 6.8, 0.05 M). The pellets were then redissolved in 10 ml of phosphate buffer and used for colour reduction experiments.

Effluent samples, neutralized to pH 7.0+0.2, were taken in 500 ml aliquots in shake flasks and inoculated with the above prepared pellets in a ratio of 1:1. All the flasks were incubated at 37° C./120 rpm for 3 days. Controls were also maintained, which did not contain any added inoculum, apart from the indigenous flora.

Samples were analyzed for colour levels using the NCASI spectrophotometric assay and percentage reduction calculated. Only two consortia exhibited colour reduction more than 50% (Table 2).

EXAMPLE III

Optimum inoculum size for reducing the colour levels was checked by inoculating the consortia in three different ratio, viz., 1:1, 1:0.5, and 1:0.75 (effluent:culture).

100 ml effluent samples were taken in shake flasks and inoculated with the formulated consortia prepared from 100 ml, 50 ml and 75 ml NB aliquots. All the conditions of incubation temperature, time and shaking were kept similar to example 2 and colour levels measured after treatment for three days.

The consortia exhibited the highest colour reduction with 1:1 effluent:biomass ratio (Table 3).

EXAMPLE IV

To improve the colour removal efficiency, fresh bacterial isolation was carried out from activated sludge obtained from ETP of a Pulp and Paper Mill. 5.0 grams of homogenised activated sludge taken from ETP of pulp and paper mill was enriched in medium consisting of 100 ml of sludge infusion, 25 ml of sterile nutrient broth and 0.1% (w/v) each of lignin (Alkali lignin-Aldrich, USA), vanillin and tannin (Sigma). The pH was adjusted to 6.8±0.2.

Individual bacteria were screened for their capacity to decolorize the paper mill effluent.

Treatability assay was conducted in 100 ml aliquots and individual bacterial pellets screened for their colour removal efficiencies. Isolate number 4 was observed to be the best among all, giving 68% colour removal in 48 hours, followed by isolate numbers, 35 (63%) and 19 (60%) (Table 4).

EXAMPLE V

Isolates 4, 19 and 35 were then cultivated individually in two different media—Nutrient Broth (NB) (rich media) and Mineral Salts Medium (minimal medium) with inorganic constituents and glucose (1%) as carbon-source to compare the effect of growth media on the performance of the cultures in removing colour for pulp mills wastewaters.

The above isolates were also cultured separately for formulating them together in the form of a consortium and test the same for the effect of culture media on consortial efficiency to reduce colour.

Nutrient Broth (NB) was prepared by dissolving (per litre), 5.0 g peptic digest of animal tissue, 5.0 g of sodium chloride, 1.5 g of beef extract, 1.5 g of yeast extract and 0.2 ml Tween-80. Mineral Salts Medium (MSM) was prepared as described in example I. Glucose (1% v/v) taken from its sterile stock solution was also added to MSM to act as a carbon supplement for the bacteria.

Colour removal assays were conducted in batch cultures in 100 ml aliquots with an incubation temperature of 37° C. and 120 rpm shaking. Samples for colour analysis were withdrawn at zero, 24 and 48 hours intervals and analyzed for color levels.

Both NB as well as MSM grown cultures exhibited almost similar results (Table 5).

EXAMPLE VI

Isolates 4, 19 and 35, which exhibited more than 60% reduction in colour of the pulp mill effluent, were formulated into a consortium and screened along with other formulated consortia which contained randomly combined cultures, for their colour reduction abilities Consortia CC17 was the best among all exhibiting up to 55% colour reduction within 48 hours.

EXAMPLE VII

The consortium CC 17 formulated in Example VI was used for colour removal of century inlet effluent in the presence of different concentrations of glucose and sucrose Viz. 0.5, 0.75, 1.0% w/v.

1% glucose was found to be the best supplement as compared to the others giving up to 75% reduction in colour within 48 hours. However, all others were not significantly different from each other (Table 7).

EXAMPLE VIII

Although addition of glucose in the wastewater seemed to be giving better colour reduction, however, its practical feasability is questionable. Hence the inventors decided to increase the biomass loading in the effluent to see the effect. Bacterium no. 4, 19 and 35 were grown individually, as described earlier till an OD 650 of 1.5–2.0, instead of 1.0 to formulate the consortium and MTCC 5099 was cultured individually to an optical density of 1.5–2.0 as well to see any enhancement in the colour removal efficiency. All the other experimental conditions were the same. Bacterium number 4 exhibited up to 55% colour reduction within 24 hours (Table 8).

The total lignin levels of the above bacteria were also estimated using the Modified Pearl Benson Method.

Bacterium number 4 exhibited the best response than the other individual bacteria as well as the consortium with the increased biomass loading. Results were replicated thrice.

EXAMPLE IX

Monitoring of biomass levels and viability of isolate 4 throughout the experiment in terms of Colony Forming Units (CFU/ml) was carried out.

It was found that at the zero hour, the CFU/ml level was approximately $10^9$ CFU/ml, which remained as such till 24 hours and in fact showed an increase to $10^{10}$ CFU/ml showing that the cells were completely viable even till the end of the experiment. Samples were streaked on solid nutrient medium to match the morphological characters of the original culture with the culture in the effluent and found to be the same.

TABLE 1

Reduction in Colour of Century Pulp and Paper Mill Inlet to ETP

| S. No. | Isolate No. | % Reduction in Colour (5 th Day) |
|---|---|---|
| 1 | 176 | 51* |
| 2 | 177 | 56* |
| 3 | 178 | 35 |
| 4 | 180 | 52* |
| 5 | 183 | 53* |
| 6 | 185 | 55* |
| 7 | 186 | 57* |
| 8 | 188 | 50* |
| 9 | 190 | 36 |
| 10 | 191 | 38 |
| 11 | 193 | 38 |
| 12 | 195 | 50* |
| 13 | 200 | 49 |
| 14 | 201 | 50* |
| 15 | 202 | 50* |
| 16 | 205 | 40 |
| 17 | 206 | 46 |
| 18 | 207 | 46 |
| 19 | 208 | 46 |
| 20 | 209 | 55* |
| 21 | 210 | 40 |
| 22 | 211 | 38 |
| 23 | 218 | 40 |
| 24 | 222 | 40 |
| 25 | 223 | 40 |
| 26 | 225 | 60* |
| 27 | 236 | 42 |
| 28 | 243 | 22 |
| 29 | 245 | 50* |
| 30 | 248 | 32 |
| 31 | 252 | 40 |
| 32 | 262 | 30 |
| 33 | 270 | 22 |
| 34 | 271 | 21 |
| 35 | 239 | 27 |

*Bacteria showing more than 50% color reduction
Note:
All values are means of three experiments

TABLE 2

% Color Reduction of Century ETP Inlet Effluent by Different Formulated Consortia

| | | Colour Removal (%) | |
|---|---|---|---|
| S. No. | Consortium | 0-day | 3rd-day |
| 1 | L1 | 36 | 57 |
| 2 | L2 | 48 | 51 |
| 3 | C2 | 39 | 63 |
| 4 | C3 | 41 | 60 |
| 5 | C5 | 51* | 58 |
| 6 | C6 | 30 | 63 |
| 7 | C7 | 60* | 60 |
| 8 | C8 | 35 | 57 |
| 9 | C9 | 48 | 58 |
| 10 | Control | Nil | Nil |

*Consortia exhibiting more than 50% on the O day.
All values are a mean of triplicate analyses with an S.D. of ±0.2

TABLE 3

% Colour reduction reduction of Century ETP inlet effluent by different formulated consortia

| S. No. | Consortia Number | % Reduction in colour after 3 days | | |
|---|---|---|---|---|
| | | 1:1 | 1:0.75 | 1:0.5 |
| 1 | L1 | 56 | 51 | 45 |
| 2 | L2 | 52 | 48 | 39 |
| 3 | C2 | 65 | 53 | 38 |
| 4 | C3 | 61 | 50 | 46 |
| 5 | C5 | 59 | 49 | 40 |
| 6 | C6 | 60 | 51 | 37 |
| 7 | C7 | 60 | 50 | 35 |
| 8 | C8 | 55 | 43 | 29 |
| 9 | C9 | 55 | 44 | 25 |
| 10 | Control | Nil | Nil | Nil |

All values are a mean of triplicate analyses with an S.D. of ±0.2

TABLE 4

% Removal of Colour by Different Bacterial Isolates After 48 Hours

| Culture No. | % Reduction in Colour |
|---|---|
| 4 | 68 |
| 18 | 55 |
| 25 | 58 |
| 32 | 55 |
| 33 | 51 |
| 34 | 51 |
| 35 | 63 |
| 36 | 51 |
| 22 | 48 |
| 20 | 56 |
| 19 | 60 |
| Control | Nil |

All values are a mean of triplicate analyses with an S.D. of ±0.2

TABLE 5

% Reduction in Colour from pulp mill effluent by Individual Isolates and their formulated consortium

| Isolate No. | 24 hrs | | 48 hrs | |
|---|---|---|---|---|
| | NB-grown | MSM grown | NB-grown | MSM grown |
| 4 | 58 | 56 | 68 | 67 |
| 19 | 49 | 48 | 61 | 60 |
| 35 | 49 | 46 | 58 | 59 |
| CC17 | 48 | 46 | 49 | 51 |

All values are average of triplicate analyses with an S.D. of ±0.2

TABLE 6

% Reduction of Colour of Pulp Mill Effluent by Different Formulated Consortia

| S. No. | Consortia No. | % Reduction in Colour | | | |
|---|---|---|---|---|---|
| | | 24 hrs | 48 hrs | 72 hrs | 96 hrs |
| 1. | CC1 | 17 | 22 | 53 | 53 |
| 2. | CC2 | 11 | 24 | 39 | 41 |
| 3. | CC3 | 11 | 26 | 48 | 50 |
| 4. | CC4 | 11 | 29 | 42 | 43 |
| 5. | CC5 | 11 | 24 | 32 | 41 |
| 6. | CC6 | 10 | 19 | 22 | 29 |
| 7. | CC7 | 9 | 5 | 12 | 33 |
| 8. | CC8 | 6 | 13 | 15 | 27 |
| 9. | CC9 | 10 | 23 | 27 | 44 |
| 10. | CC10 | 1 | 1 | 9 | 8 |
| 11. | CC11 | 0 | 11 | 16 | 8 |
| 12. | CC12 | 3 | 10 | 15 | 40 |
| 13. | CC13 | 18 | 52 | 52 | 65 |
| 14. | CC14 | 7 | 8 | 8 | 13 |
| 15. | CC15 | 15 | 30 | 30 | 66 |
| 16. | CC16 | 5 | 14 | 14 | 18 |
| 17. | CC17 | 47 | 55 | 62 | 70 |

All values are average of triplicate analyses with an S.D. of ±0.2

TABLE 7

Effect of Additional Carbon Sources on the Efficiency of Consortium CC17

| S. No. | Sample | % Removal of Colour | | |
|---|---|---|---|---|
| | | 24 hours | 48 hours | 72 hours |
| 1. | Effluent + Consortia | 49 | 63 | 72 |
| 2. | Effluent + Consortia + 0.5% Glucose | 60 | 68 | 73 |
| 3. | Effluent + Consortia + 0.75% Glucose | 62 | 69 | 71 |
| 4. | Effluent + Consortia + 1.0% Glucose | 68 | 75 | 79 |
| 5. | Effluent + Consortia + 0.5% Sucrose | 60 | 65 | 73 |
| 6. | Effluent + Consortia + 0.75% Sucrose | 64 | 73 | 75 |
| 7. | Effluent + Consortia + 1.0% Sucrose | 63 | 74 | 75 |

All values are average of duplicate analyses with an S.D. of ±0.2

TABLE 8

Effect of Increasing Biomass Levels of Bacteria Individually as well as in the Form of Consortia on Colour and Total Lignin Levels of Pulp Mill Effluent

| Sample | % Reduction in Colour | | % Reduction in Total Lignin | |
|---|---|---|---|---|
| | 24 hours | 48 hours | 24 hours | 48 hours |
| Effluent + CC17 | 50 | 58 | 16 | 19 |
| Effluent + MTCC 5099 | 55 | 60 | 18 | 25 |
| Effluent + Bacterium 19 | 48 | 49 | 19 | 29 |
| Effluent + Bacterium 35 | 43 | 48 | 26 | 31 |

All values are an average of three readings with an S.D. of ±0.5

TABLE 9

Viability of MTCC 5099 in the Effluent during the colour reduction experiment in terms of Colony Forming Units (CFU/ml)

| CFU/ml (0 hour) | CFU/ml (24 hours) | CFU/ml (48 hour) |
|---|---|---|
| $9.7 \times 10^9$ | $8.0 \times 10^9$ | $6.1 \times 10^{10}$ |

Advantages

1. The isolated bacterium is capable of reducing the colour of the pulp mill effluent in a reproducible manner.
2. The isolated bacterium remains viable even after the completion of the experiment suggesting its reusability in next set of experiment.
3. The naturally isolated bacterium is non pathogenic and can be cultured on simple nutrient media without any economic burden.
4. This kind of bacterial reduction of colour from pulp mill effluents is novel.

What is claimed is:

1. An aerobic process for the reduction of colour from pulp mill effluent using a gram -ve bacterium strain of Accession No. MTCC 5099, which comprises:
    a) inoculating in a flask appropriate aliquots of a pulp and paper mill effluent with a cell slurry comprising a gram -ve bacterium strain of Accession No. MTCC 5099, for colour reduction studies along with a control flask containing effluent sample without any added inoculum;
    b) incubating the flasks set up in step (a) at 37° C./100 rpm for 48 hours;
    c) withdrawing samples from the above flasks in 50 ml aliquots and processing them for assessing colour and total lignin levels,
    d) analysing the colour removal efficiency of the above said bacterium by comparing the colour levels of the effluent treated with the bacterium with the colour level of control sample after 24 and 48-hour intervals,
    e) checking the viability of the above said culture in the effluent by culturing the same on nutrient agar medium and calculating CFU/ml.

2. A process as claimed in claim 1, wherein the viability of the above said culture is checked by plating dilutions of sample taken from the experiment to obtain countable colonies and calculating CFU/ml of the same after 24 and 48 hour intervals.

3. A process as claimed in claim 1 wherein the aerobic, biological decolorization process further comprises a bacterial isolate, obtained from activated sludge of a pulp and paper mill ETP, which gives up to 55% reduction in colour levels of the given effluent.

4. A process as claimed in claim 1, wherein the strain shows color reduction of 55% in 24 hrs.

5. A process as claimed in claim 1, wherein the strain shows color reduction of 60% in 48 hrs.

6. A process as claimed in claim 1, wherein the ratio of equivalent to biomass is about 1:1.

7. A process as claimed in claim 1, wherein the strain is viable after the color reduction.

* * * * *